United States Patent [19]

Junge et al.

[11] Patent Number: 4,536,493

[45] Date of Patent: Aug. 20, 1985

[54] SATURATED AMINOCYCLITOL DERIVATIVES, THEIR PREPARATION AND MEDICAMENTS CONTAINING THESE COMPOUNDS

[75] Inventors: Bodo Junge, Wuppertal, Fed. Rep. of Germany; Lutz Müller, Elkhart, Ind.

[73] Assignee: Baker Aktiengesellschaft, Leverkusen, Fed. Rep. of Germany

[21] Appl. No.: 385,222

[22] Filed: Jun. 4, 1982

[30] Foreign Application Priority Data

Jun. 13, 1981 [DE] Fed. Rep. of Germany ....... 3123520

[51] Int. Cl. .................... A61K 31/70; C07G 11/00
[52] U.S. Cl. .................... 514/25; 536/17.9; 536/16.8; 536/18.1
[58] Field of Search .................... 536/17.9, 16.8, 18.1; 424/180

[56] References Cited

U.S. PATENT DOCUMENTS 4,175,123  11/1979  Junge et al. ..................... 536/55 X

FOREIGN PATENT DOCUMENTS

| 2375248 | 7/1978 | France . |
| 0024397 | 2/1982 | Japan . |
| 2011397 | 7/1979 | United Kingdom . |
| 2060629 | 5/1981 | United Kingdom . |

OTHER PUBLICATIONS

Onoto et al., Journ. of Antibiotics, vol. 34(11), pp. 1429–1433, (Jun., 1981).

*Primary Examiner*—Ethel G. Love
*Attorney, Agent, or Firm*—Sprung, Horn, Kramer & Woods

[57] ABSTRACT

The invention relates to saturated aminocyclitol derivatives, as defined herein in Formula (F). Also included in the invention are methods for preparing said saturated aminocyclitol derivatives, compositions containing said saturated aminocyclitol derivatives and methods for the use of said compounds and compositions to provide inhibition of $\alpha$-glycoside hydrolases.

15 Claims, No Drawings

SATURATED AMINOCYCLITOL DERIVATIVES, THEIR PREPARATION AND MEDICAMENTS CONTAINING THESE COMPOUNDS

The present invention relates to certain novel saturated aminocyclitol derivatives, to a process for their production and to their use as medicaments, in particular as agents against diabetes, hyperlipaemia and obesity.

According to the present invention there are provided compounds which are saturated aminocyclitol derivatives of the formula

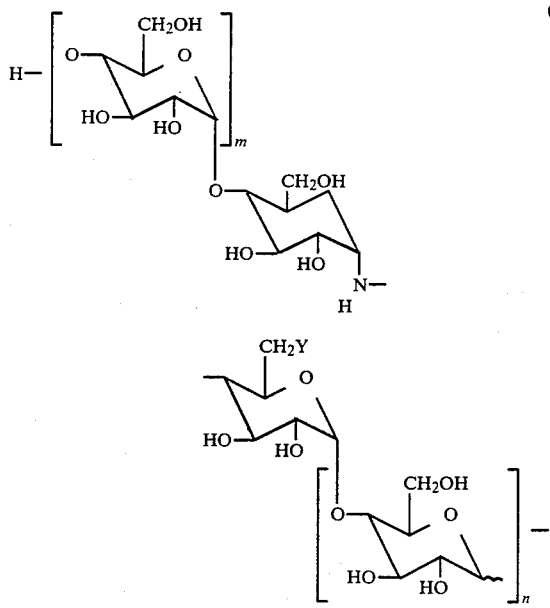

in which
m and n independently of each other denote 0 or an integer from 1 to 8 and the sum of m+n has a value from 0 to 8,
X represents OH, OR, SH, SR, $NH_2$, NHR or $NRR_1$, and
R and $R_1$ independently represent an optionally substituted alkyl, carbocyclic, aryl, aralkyl or heterocyclic radical (the last bonded via a carbon atom of the heterocyclic system or of a benzene nucleus fused thereto or via a —$CH_2$— bridge outside the ring) or, together with the nitrogen atom to which they are bonded, form a heterocyclic ring, and
Y represents H or OH.

Preferred compounds according to the present invention are those in which m and n are independently 0, 1, 2 or 3, and particularly preferred compounds are those in which m is 0 and n is 2 or 0. Further preferred compounds are those in which X represents OH or OR, and those in which Y represents H.

If R denotes an alkyl group, it preferably represents a straight-chain or branched alkyl group with 1 to 30 in paraticular 1 to 18, especially 1 to 8, carbon atoms. Examples which may be mentioned are methyl, ethyl, n-propyl, i-propyl, n-butyl, n-hexyl, n-octyl, oct-2-yl, docecyl, lauryl, cetyl and stearyl.

The alkyl groups can carry one or more, preferably 1,2,3,4 or 5 identical or different substituents. Examples of substituents which may be mentioned are: hydroxyl, alkoxy with preferably 1 to 4 carbon atoms (in particular methoxy and ethoxy), amino, monoalkylamino and dialkylamino with preferably 1 to 4 carbon atoms per alkyl radical (in particular monomethylamino, monoethylamino, dimethylamino and diethylamino), mercapto, alkylthio with preferably 1 to 4 carbon atoms (in particular methylthio and ethylthio), halogen (preferably fluorine, chlorine, and bromine) alkylcarbonyl with preferably 1 to 4 carbon atoms in the alkyl radical, carboxyl, nitro, cyano, an aldehyde group and a sulphonic acid group.

It may be mentioned that, if R denotes a substituted alkyl group, preferred compounds according to the present invention are also those in which R is a substituted alkyl group derived from sugar derivatives as are for example polyalcohols or sugar acids derived from sugars as for example D-Glucose, D-Mannose or D-Fructose.

If R denotes a saturated or unsaturated carbocyclic group, it preferably represents a saturated or unsaturated carbocyclic radical which has 3 to 7 carbon atoms and can be substituted, suitable substituents being those groups and atoms mentioned above for the open-chain alkyl groups. If R denotes a saturated or unsaturated carbocyclic group, preferred compounds according to the present invention are also those in which R represents a saturated or unsaturated cyclitol radical.

If R denotes an aryl group or an aralkyl group, it preferably represents a group with a mono- or bi-cyclic carbocyclic aromatic radical which has 6–10 carbon atoms in the aryl part, in particular phenyl, and which can be substituted.

The aryl radicals can carry one or more, preferably 1, 2 or identical or different substituents. Examples of substituents which may be mentioned are: alkyl with 1 to 10 carbon atoms, which, in turn, can be substituted by, for example, chlorine, nitro or cyano; hydroxyl, alkoxy with preferably 1 to 4 carbon atoms; amino, mono-alkylamino and dialkylamino with preferably 1 to 4 carbon atoms per alkyl radical; mercapto, alkylthio with preferably 1 to 4 carbon atoms; carboxyl and carbalkoxy with preferably 1 to 4 carbon atoms, in the alkyl group, a sulphonic acid group, arylsulphonyl (preferably phenylsulphonyl); aminosulphonyl-, alkyl- amino- and dialkylaminosulphonyl with 1 to 4 carbon atoms per alkyl group (preferably methyl- and dimethylaminosulphonyl); nitro, cyano or the aldehyde group; alkylcarbonylamino with preferably 1 to 4 carbon atoms in the alkyl group; alkylcarbonyl with 1 to 4 carbon atoms in the alkyl group, benzoyl, benzylcarbonyl and phenylethylcarbonyl, the last-mentioned alkyl, phenyl, benzyl and phenylethyl radicals themselves again possibly being substituted by, for example, chlorine, nitro or hydroxyl. If R denotes an aralkyl group the aryl radical is preferably attached to a saturated or unsaturated chain of up to 6 carbon atoms. Such aralkyl groups are for example benzyl, phenethyl, phenylpropyl or cinnamyl.

Preferred heterocyclic radicals R are derived from heteroparaffinic, heteroaromatic or heteroolefinic 5- or 6-membered rings which preferably 1 to 3 identical or different heteroatoms selected from oxygen, sulphur and nitrogen. These ring systems can carry further substituents such as hydroxyl, amino or $C_1$–$C_4$-alkyl groups, or can be fused with benzene nuclei or further, preferably 6-membered, heterocyclic rings of the type mentioned.

A preferred example of a heterocyclic radical R bonded via a —CH$_2$— bridge outside the ring is the furfuryl radical.

R$_1$ preferably represents a straight-chain or branched alkyl group with 1 to 6 carbon atoms, a benzyl or phenyl group, each of which are unsubstituted or substituted, preferably by alkoxy with 1 to 4 carbon atoms, amino, C$_1$ to C$_4$ monoalkylamino and C$_1$ to C$_4$ dialkylamino, nitro, halogen, cyano, hydroxyl, nitro, mercapto, C$_1$ to C$_4$ thioalkyl, a carboxyl or sulphonic acid group and, if R$_1$ denotes a phenyl group, also by C$_1$ to C$_4$ alkyl.

As stated above, R and R$_1$ can also together, with inclusion of the nitrogen atom to which they are bonded, form a heterocyclic ring.

This ring can be saturated or unsaturated and can contain 1 to 3 further, preferably 1, oxygen, sulphur or nitrogen atom and as hetero groups preferably an SO$_2$- or N-alkyl group, the alkyl group of the N-alkyl group preferably containing 1 to 4, in particular 1 or 2 carbon atoms. Methyl, ethyl, n- and i-propyl and n-, i- and t-butyl may be mentioned as such alkyl groups. The heterocyclic ring can contain 5 to 7, preferably 5 or 6, ring members. A 6-membered heterocyclic ring preferably contains the heteroatom or the heterogroup in the paraposition to the nitrogen atom. Examples of the heterocyclic ring which may be mentioned are pyrrolidine, piperidine, piperazine, hexamethyleneimine, morpholine and N-methylpiperazine.

It is surprising that the saturated aminocyclitol derivatives according to the present invention are potent inhibitors for α-glycoside hydrolases, in particular disaccharidases of the digestive tract. Admittedly, it is known from a number of publications (e.g. from DE-OS (German Published Specification) No. 2,347,782; DE-OS (German Published Specification) No. 2,614,393; U.S. Pat. No. 4,175,123; U.S. Pat. No. 4,197,292; DE-OS (German Published Specification) No. 2,855,409 and Naturwissenschaften 64, 535 (1977)) that unsaturated compounds with a double bond in the cyclitol part of the molecule analogous to the compounds of the formula (I) are effective inhibitors for α-glycoside hydrolases. According to the "transition state analogue" theory for enzyme inhibitors (Lindquist, R. N.: Medicinal Chemistry, Vol. 11 (V), p. 24 (Ariens, E. J. ed), New York - San Francisco - London: Academic Press 1975), however, it had to be assumed that the double bond in these compounds is a structural feature essential for the activity, because only the *unsaturated* cyclitol unit resembles in its half-chair conformation the glycosyl cation in half-chair conformation formed during the enzymatic reaction from the substrate (sucrose, maltose or starch).

It is thus even more surprising that the saturated aminocyclitol derivatives according to the invention with an α-D-gluco configuration in the cyclitol part show a strong inhibitory activity similar to that of the unsaturated compounds.

The compounds according to the present invention, because of their enzyme inhibitory activity, can be used to delay or block digestion of carbohydrates in warm-blooded animals. Thus they are valuable for the treatment of metabolic diseases, such as diabetes, hyperlipaemia and obesity, and hence enrich the range of medicaments.

According to the present invention there is further provided a process for the production of a compound according to the present invention in which an unsaturated compound of the formula

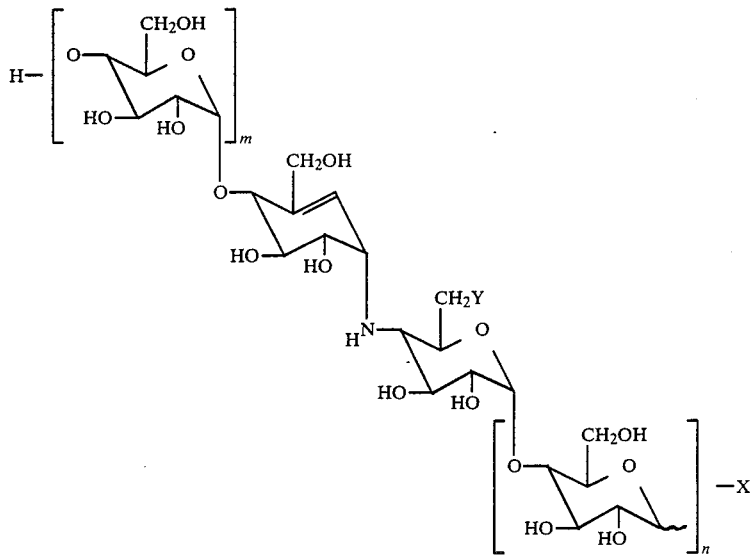

II in which X, Y, n and m have the abovementioned meanings, is hydrogenated, catalytically or using suitable microorganisms.

The compounds of formula (II) are described in the German Offenlegungsschriften and other publications quoted above.

On catalytic hydrogenation, the compounds of the present invention are generally obtained only as mixtures with other products of hydrogenolysis and hydrogenation. Particularly important side-reactions are the hydrogenolytic cleavage of the C-N bond and the C-O bonds in the allylic position to the double bond, and the saturation of the double bond to saturated compounds with L-ido configuration in the cyclitol part. Thus the compounds of the present invention must generally be isolated by chromatograhic separation procedures from the hydrogenation mixture.

The customary transition metal catalysts (such as Pt, Pd/C or Ni) are generally used as catalysts for the hydrogenation. The preferred solvents are water or water-/alcanol mixtures. The alcanols should be water-miscible. Preferred alcanols are methanol and ethanol. The hydrogenation is carried out preferably at room temperature and under a pressure of between 1 and 100 atmospheres, preferably under a pressure of between 1 and 3 atmospheres of $H_2$.

The process according to the present invention is illustrated by the following equation:

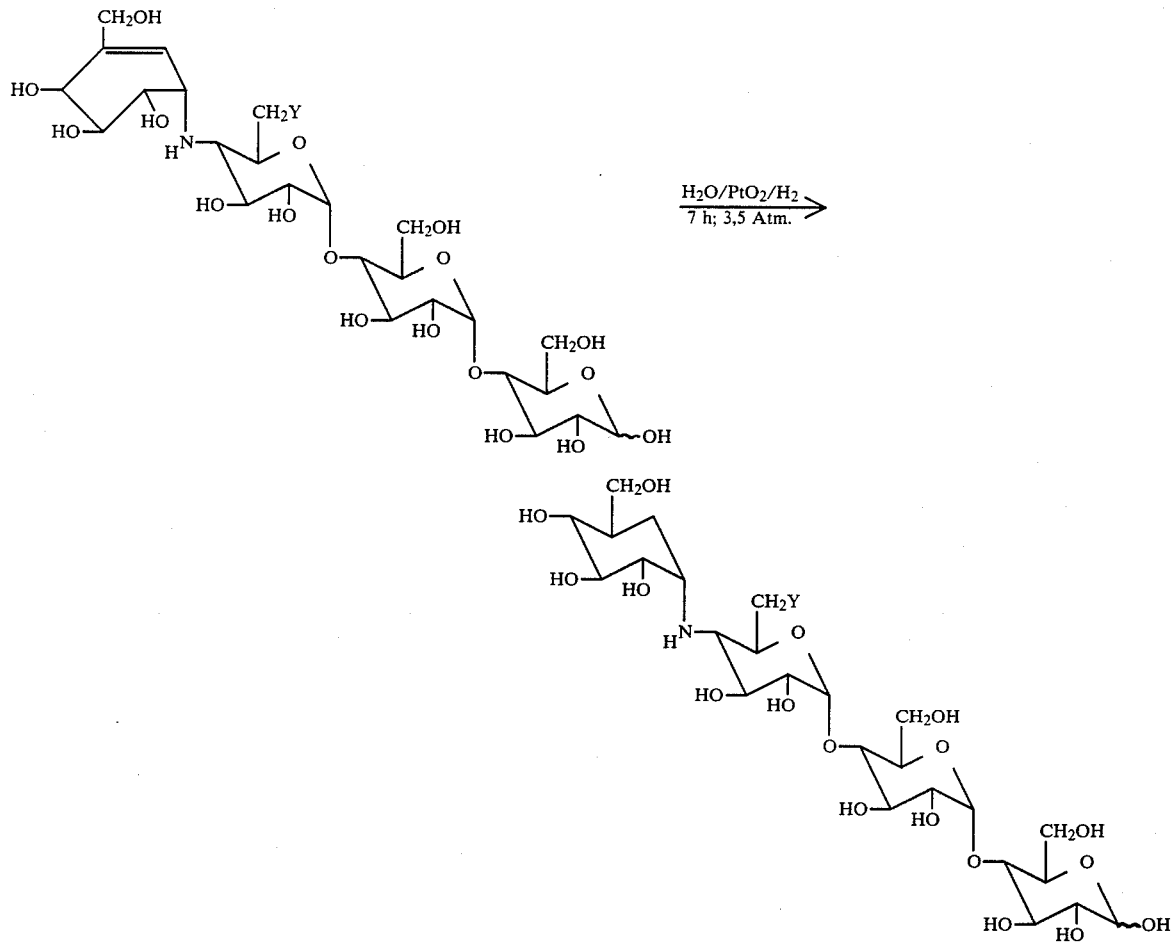

It is known that hyperglycaemia occurs, in warm-blooded animals, after ingestion of basic and luxury foodstuffs containing carbohydrates (e.g. grain starch, potato starch, fruit, fruit juice, beer and chocolate), and is brought about as a result of a rapid degradation of the carbohydrates by glycoside hydrolases (e.g. salivary and pancreatic amylases, maltases and saccharases) in accordance with the following scheme:

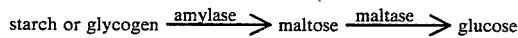

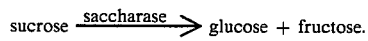

This hyperglycaemia is particularly severe and long-lasting in diabetics. In obese persons, the alimentary hyperglycaemia frequently produces a particularly strong secretion of insulin which, for its part, leads to increased synthesis and decreased degradation of fat. Following this type of hyperglycaemia, hypoglycaemia frequently occurs in persons with healthy metabolism and in obese persons as a result of the secretion of insulin. It is known that both hypoglycaemia and also chyme lingering in the stomach promote the production of gastric fluid, which itself initiates or favours the genesis of gastritis or a gastric or duodenal ulcer.

The inhibitors of the glycoside hydrolases according to the invention can substantially decrease the alimentary hyperglycaemia, hyperinsulinaemia and hypoglycaemia after challenge with wheat starch or sucrose or maltose, and can accelerate the passage through the stomach of these carbohydrates mentioned.

Furthermore, the conversion of carbohydrates into lipids of the fatty tissue and the incorporation of alimentary fat into the depot fatty tissue is decreased or delayed.

Furthermore, it is known that in the cavity of the mouth, carbohydrates, particularly sucrose, are cleaved by micro-organisms and thus promote the formation of caries.

For this reason, inhibitors of the glycoside hydrolases are suitable as therapeutics for the following indications: obesity, hyperlipaemia (atherosclerosis), diabetes, pre-diabetes, gastritis, gastric ulcer, duodenal ulcer and caries.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile aqueous solution.

The invention also provides a medicament in dosage unit form comprising a compound of the invention.

The invention also provides a medicament in the form of tablets (including lozenges and granules), dragees, capsules, pills or ampoules comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to fortieth) of a daily dose or the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of solutions, suspensions, syrups, granulates or powders.

Particularly preferred medicaments for administration are tablets, coated tablets, capsules, solutions, suspensions, granulates, chewing gum, toothpaste and as additives to basic and/or luxury foods containing carbohydrates.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The pharmaceutical compositions which are solutions and emulsions can, for example, contain the customary diluents (with, of course, the abovementioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide oils (for example ground nut oil), glycerol, tetrahydrofurfuryl alcohol, polyethylene glycols and fatty acid esters of sorbitol or mixtures thereof.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention. Combinations of the active compounds according to the invention with known oral antidiabetic agents ($\beta$-cytotropic sulphonylurea derivatives and/or blood-sugar active biguanides) are advantageous.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granules), pills, dragees, capsules and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally.

In general it has proved advantageous to administer peroral amounts of from 1 to 10,000 SIU (as defined hereinbelow) per kg of body weight per day, once or several times daily before and/or during and/or after meals or drinks, to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered, as indicated, it can be advisable to divide these into several individual administrations over the course of the day.

The following Examples 1 and 2 illustrate the production of compounds according to the present invention.

EXAMPLE 1

(Production of a compound of the formula (I) with m=0, n=2, Y=H and X=OH)

5 g of acarbose (a compound of the formula (II) with m=0, n=2, Y=H and X=OH) were hydrogenated in 200 ml of water with 2.5 g of $PtO_2$ as the catalyst for 7 hours under a pressure of 3.5 atmospheres of $H_2$ at room temperature. Then the catalyst was filtered off, the solution was concentrated on a rotary evaporator and applied to a column (40×2.4 cm) filled with "Dowex" 50 W-X 4 (Trade Mark): $H^{\oplus}$ form. The non-basic hydrogenolysis products were first eluted with water. Fractions of approx. 7 ml were taken. From fracton 70, the basic hydrogenolysis and hydrogenation products were eluted with 0.025 N HCl. Fractions 515–536 were combined, neutralised with basic exchanger ("Amberlite" IRA 410 (Trade Mark); $OH^{\ominus}$ form), and concentrated on a rotary evaporator. 100 mg of the compound of the formula (I) with m=0, n=2 and X=OH were obtained.

The substance was characterised by a proton resonance spectrum at 250 MHz in $D_2O$.

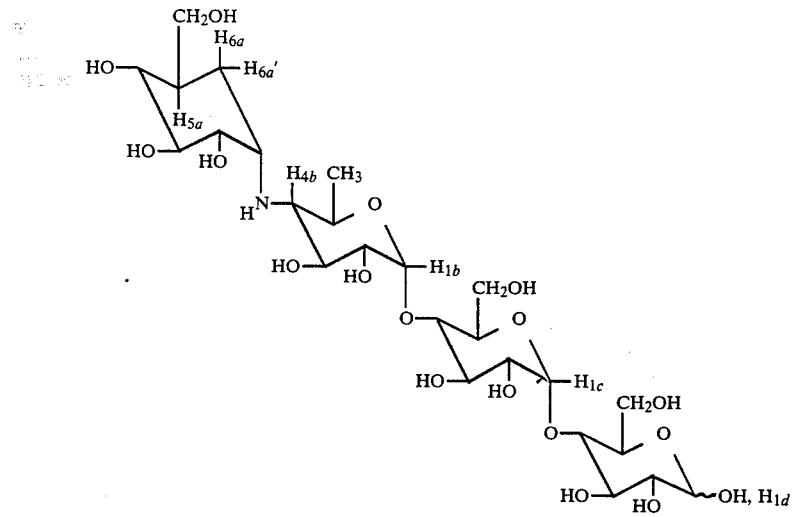

The following shift values can be obtained from the spectrum (H O D/at $\delta$=4.67 ppm):

| Proton | $\delta$ (ppm) | Form of signal |
| --- | --- | --- |
| $H_{6a}$ | 1.23 | doublet (J~3Hz) of triplets (J~11-14 Hz) |
| $H_{6a'}$ | 1.77 | triplet (J~3H) of doublets (J~14 Hz) |
| $H_{5a}$ | 1.65 | broad signal |

| Proton | $\delta$ (ppm) | Form of signal | |
| --- | --- | --- | --- |
| $H_{4b}$ | 2.26 | | triplet (J~10 Hz) |
| $H_{1d}(\beta)$ | 4.50 | $\beta/\alpha$ ratio 2:1 | doublet (J = 8 Hz) |
| $H_{1d}(\alpha)$ | 5.08 | | doublet (J = 3.5 Hz) |
| $H_{1c}$ | | | two doublets (J~3-4 Hz) at 5.16 and 5.25 |
| $H_{1b}$ | | | |
| $CH_3$-group | 1.16 | | doublet (J = 6.3 Hz) |

EXAMPLE 2

(Production of a compound of the formula (I) with m=0, n=0, Y=H and X=$OCH_3$)

5 g of the compound of the formula (II) with m=0, n=0 and X=$OCH_3$ ($\alpha/\beta$ mixture) were hydrogenated in 250 ml of water with 2.5 g of $PtO_2$ as the catalyst for 7 hours under a pressure of 3.5 atmospheres of $H_2$ in a shaken flask at room temperature. The catalyst was filtered off and the solution concentrated in vacuo. The aqueous residue was put onto a column filled with "Amberlite" IR 120 ($H^{\oplus}$ form). The column was first eluted with water and then with 4% strength aqueous ammonia. The aqueous eluate was discarded and the ammoniacal eluate was concentrated to dryness on a rotary evaporator. The residue was chromatographed on two Merck silica gel pre-packed columns size C, arranged in series. Acetic acid/MeOH/$H_2O$/25% strength $NH_3$ in a ratio of 100/60/20/2 was used as the mobile phase. Fractions of approx. 5 ml were collected. Fractions 163 to 200 provided 276 mg of not quite pure compound of the formula (I) with m=0, n=0 and X=$OCH_3$. This was chromatographed over a Merck silica gel pre-packed column size B for further purification. Ethyl acetae/MeOH/$H_2O$/25% strength $NH_3$ in a ratio of 100/50/10/1 was used as the mobile phase. 12 mg of the compound of the formula (I) with m=0, n=0 and X=$OCH_3$ was obtained as an $\alpha/\beta$ mixture.

The substance was characterised by a proton resonance spectrum at 250 MHz in $CD_3OD$

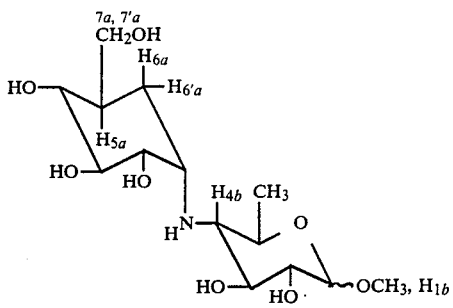

The following shift values can be obtained from the spectrum (CD$_3$OH at δ=4.78 ppm):

| Proton | δ (ppm) | | Form of signal |
|---|---|---|---|
| CH$_3$-group | 1.20 | (α) | doublet (J = 6 Hz) |
| | 1.25 | (β) | doublet (J = 6 Hz) |
| H$_{6a}$ | ~1.22 | | concealed to a large extent by the methyl group |
| H$_{6'a}$ | 1.80 | ⎫ overlap | |
| H$_{5a}$ | ~1.77 | ⎭ | |
| H$_{4b}$ | 2.19 | (β) | triplet (J~10 Hz) |
| | 2.17 | (α) | triplet (J~10 Hz) |
| —OCH$_3$ | 3.30 | (α) | singlet |
| | 3.42 | (β) | singlet |
| H$_7$ and H$_{7'}$ | ~3.56 and 3.62 | | AB system (J = 10.5 Hz) with additional splitting (J = 5.5 Hz and J$_2$ = 4 Hz) |
| H$_{1b}$(β) | 4.04 | ⎫ β/α ratio 3:1 | doublet (J = 7.5 Hz) |
| H$_{1b}$(α) | 4.53 | ⎭ | doublet (J = 3.5 Hz) |

SACCHARASE TEST

A saccharase inhibitor unit (SIU) is defined as the amount of inhibitor which inhibits two saccharase units to the extent of 50%. A saccharase unit (SU) is the amount of enzyme which cleaves 1 μmol of sucrose into glucose and fructose in one minute under the test conditions given below.

The μmol of glucose formed were quantitatively determined with the aid of the glucose oxidase reaction under conditions in which further cleavage of sucrose by saccharase did not occur. To perform the tests, 0.05 ml of a solution of saccharase[1] which had been set at 0.12 SU was mixed with 0 to 20 μg of inhibitor or 0 to 20 μl of the solution for testing and made up with 0.1 M sodium maleate buffer of pH 6.0 or 0.1 ml. The mixture was equilibrated for 10 minutes at 35° C. and then mixed with 0.1 ml of a 0.05 M solution of sucrose in 0.1 M sodium maleate buffer of pH 6.0 pre-warmed to 35° C. After incubation for 20 minutes at 35° C., the saccharase reaction was stopped by addition of 1 ml of glucose oxidase reagent[2], and incubation was continued for 30 minutes at 35° C. Thereafter 1 ml of 50% strength H$_2$SO$_4$ was added and measured at 545 nm against an appropriate blank. For evaluation, the percentage inhibition of the saccharase employed is calculated and, with the aid of a glucose calibration curve, converted from the 50% inhibition point to SIU/g or SIU/liter.

[1] Solubilised saccharase from pig small intestinal mucosa according to B. Borgström, A. Dahlquist, Acta Chem. Scand. 12, (1958), page 1997. Diluted with 0.1 M sodium maleate buffer of pH 6.0 to the appropriate SU content.

[2] The glucose oxidase reagent is prepared by dissolving 2 mg of glucose oxidase (Boehringer No. 15423) in 100 ml of 0.565 M tris-HCl buffer of pH 7.0 and subsequently adding 1 ml of detergent solution (2 g of Triton X 100+8 g of 95% strength ethanol AR), 1 ml of dianisidine solution (260 mg of o-dianisidine 0.2 HCl in 20 ml of H$_2$O) and 0.5 ml of 0.1% strength aqueous peroxidase solution (Boehringer No. 15302).

EFFECTIVENESS IN THE SACCHARASE INHIBITION TEST IN VITRO:

| | SIU/g |
|---|---|
| Example 1: | |
| Substance of the formula I with m = 0, n = 2, Y = H and X = OH | 59 829 |
| Comparison: | |
| Substance of the formula II with m = 0, n = 2, Y = H and X = OH (acarbose) | 77 700 |
| Example 2 | |
| substance of the formula I with m = 0, n = 0, Y = H and X = OCH$_3$ (α/β mixture 1:3) | 38 850 |
| Comparison: | |
| Substance of the formula II with m = 0, n = 0, Y = H and X = OCH$_3$ (α/β mixture 1:9) | 38 850 |

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to a warm-blooded animal is converted in the patient's body to the active compound.

What is claimed is:

1. A compound which is a saturated aminocyclitol derivative of the formula

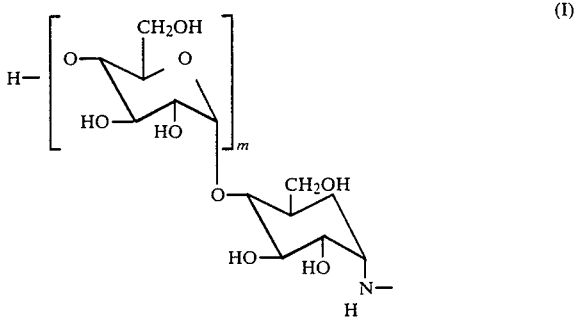

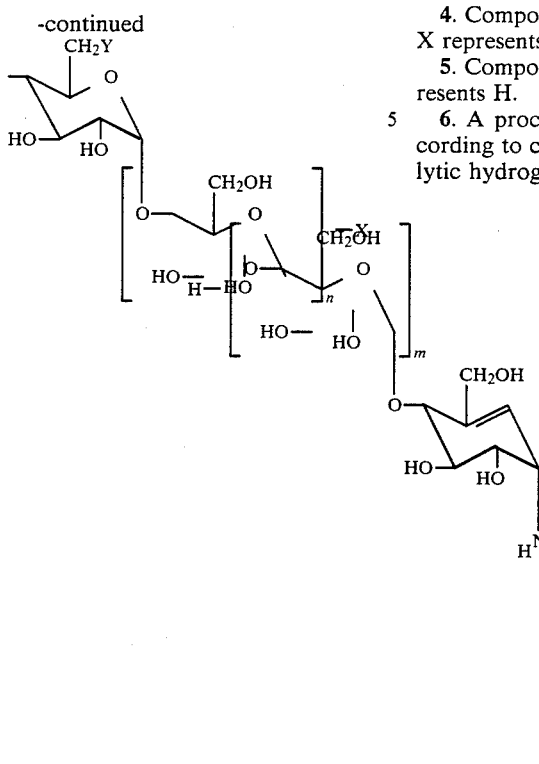

in which
- m and n independently of each other denote 0 or an integer from 1 to 8 and the sum of m+n has a value from 0 to 8,
- X represents OH, OR, SH, SR, $NH_2$, NHR or $NRR_1$, and
- R and $R_1$ independently represent a straight chain or branched, saturated or unsaturated alkyl radical with 1 to 8 carbon atoms; a saturated or unsaturated carbocyclic radical with 3 to 6 carbon atoms; an aralkyl radical consisting of an alkylen- or -alkenylen-chain having 1 to 3 carbon atoms and an optionally substituted phenyl ring with one or two substituents selected from OH, $NH_2$, Cl, $CH_3$, $NO_2$, COOH; an optionally substituted pheny ring with one or two substituents selected from -OH, -Cl, -$CH_3$, -$NO_2$, -COOH or

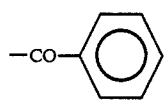

together with the nitrogen atom to which they are bonded form a heterocyclic five- or six membered ring, selected from pyrrolidine, piperidine, piperazine, hexamethyleneimine, morpholine and N-methylpiperazine.

2. A compounds according to claim 1, in which m and n independently are 0, 1, 2 or 3.

3. A compounds according to claim 1 in which m is 0 and n is 0 or 2.

4. Compounds according to claim 1, 2 or 3, in which X represents OH.

5. Compounds according to claim 4, in which Y represents H.

6. A process for the production of a compound according to claim 1 which comprises subjecting to catalytic hydrogenation a compound of the formula (II)

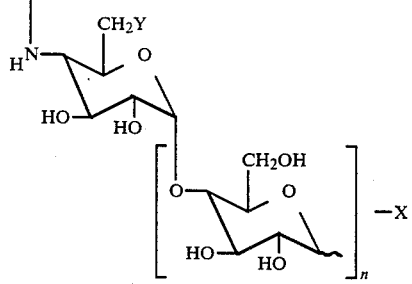

in which m, n and x have the same meanings as in claim 1.

7. A process according to claim 6 in which the hydrogenation is performed as a catalytic hydrogenation using a transition metal catalyst at room temperature and under a pressure of between 1 and 100 atmospheres of $H_2$.

8. A process according to claim 7, in which the hydrogenation is performed under a pressure of between 1 and 3 atmospheres of $H_2$.

9. A process according to claim 6, 7 or 8, in which the compound of the hydrogenation product is isolated by a chromatographic separation procedure.

10. A pharmaceutical composition for inhibiting alpha-glycoside hydrolase, containing as an active ingredient in amount of a compound according to claim 1 effective for inhibiting α-glucoside hydrolase in admixture with an inert pharmaceutical carrier.

11. A pharmaceutical composition of claim 10 in the form of a sterile aqueous solution.

12. A medicament in dosage unit form effective for inhibiting α-glucoside hydrolase comprising an α-glucoside-hydrolase-inhibiting amount of a compound according to claim 1 and an inert pharmaceutical carrier.

13. A medicament of claim 12 in the form of tablets, coated tablets, capsules, solutions, suspensions, granulates, chewing gum or toothpaste.

14. A method of inhibiting α-glycoside hydrolases in warm-blooded animals which comprises administering to the said animals in amount of an active compound according to claim 1 effective for inhibiting α-glycoside hydrolase either alone or in admixture with a diluent or in the form of a medicament.

15. A method according to claim 14 in which the active compound is administered perorally in an amount of 1 to 10,000 SIU per kg body weight per day.

* * * * *

UNITED STATES PATENT AND TRADEMARK OFFICE
CERTIFICATE OF CORRECTION

PATENT NO. : 4,536,493  Page 1 of 2
DATED : August 20, 1985
INVENTOR(S) : Bodo Junge, et al.

It is certified that error appears in the above-identified patent and that said Letters Patent is hereby corrected as shown below:

| | |
|---|---|
| Col. 1, lines 40, 41, 54, & 56; Col. 4, line 50; Col. 9, lines 18, 20, 34; Col. 10, lines 15, 16, 17, 33, 65; Col. 12, lines 20, 23, 27, 33; Col. 13, lines 40, 41; Col. 13, lines 65, 66, 67, 68; Col. 14, line 31 | Delete "m" and "n" and substitute --$m$-- and --$n$-- |
| Col. 4, line 65 | Correct spelling of "chromatographic" |
| Col. 9, line 61 | Delete "H" and substitute --$H$-- |
| Col. 10, line 36 | Correct spelling of --acetate-- |
| Col. 11, line 16 | Delete "OH" and substitute --O$H$-- |
| Col. 11, line 66 | Delete "12" and substitute --$12$-- |

UNITED STATES PATENT AND TRADEMARK OFFICE
CERTIFICATE OF CORRECTION

PATENT NO. : 4,536,493
DATED : August 20, 1985
INVENTOR(S) : Bodo Junge, et al.

It is certified that error appears in the above-identified patent and that said Letters Patent is hereby corrected as shown below:

Col. 13, line 55      Delete "-NO2" and substitute -- $-NO_2$ --

Col. 13 and Col. 14, lines 7 to 12      Delete 1st structure of formula of Claim 6 and substitute

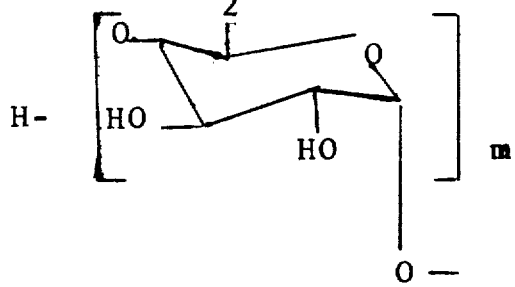

Signed and Sealed this

Thirty-first Day of December 1985

[SEAL]

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,536,493  Page 1 of 3
DATED : August 20, 1985
INVENTOR(S) : Bodo Junge, et al.

It is certified that error appears in the above-identified patent and that said Letters Patent is hereby corrected as shown below:

Col. 12, line 52    Delete Claim 1 in its entirety and substitute:

--A compound which is a saturated aminocyclitol derivative of the formula

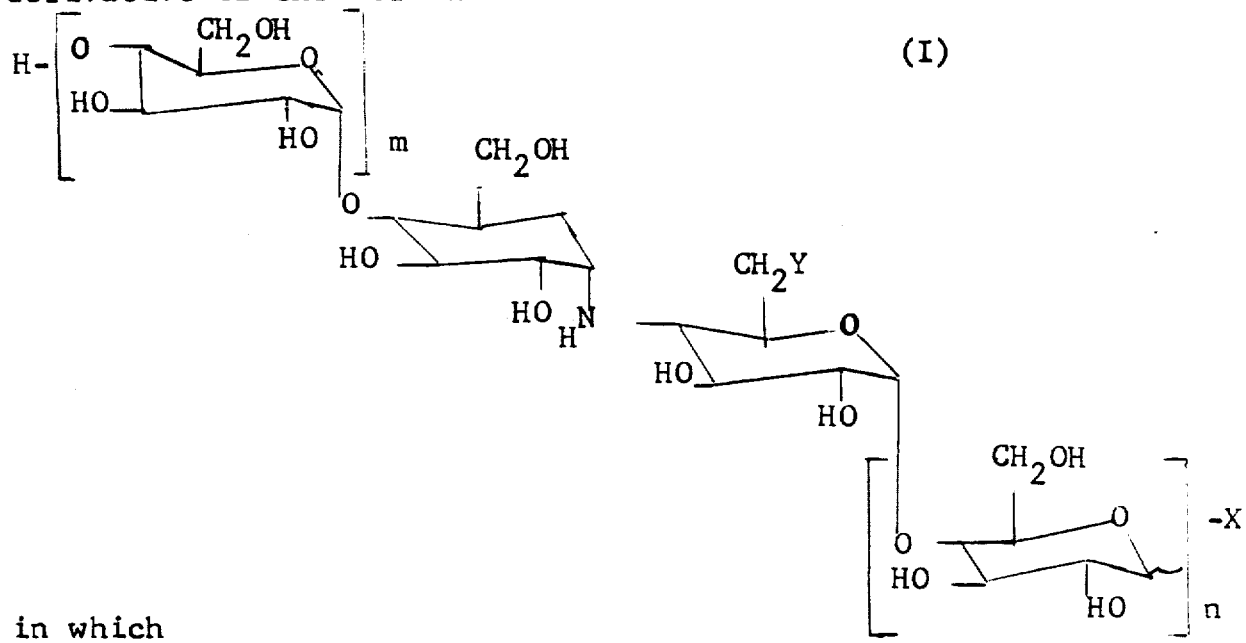

in which
  $m$ and $n$ independently of each other denote 0 or an integer from 1 to 8 and the sum of $m+n$ has a value from 0 to 8,
  X represents OH, OR, SH, SR, $NH_2$, NHR or $NRR_1$, and
  R and $R_1$ independently represent a straight chain or branched, saturated or unsaturated alkyl radical with 1 to 8 carbon atoms; a saturated or unsaturated carbocyclic radical with 3 to 6 carbon atoms; an aralkyl radical consisting of an

UNITED STATES PATENT AND TRADEMARK OFFICE
CERTIFICATE OF CORRECTION

PATENT NO. : 4,536,493
DATED : August 20, 1985
INVENTOR(S) : Bodo Junge, et al.

It is certified that error appears in the above-identified patent and that said Letters Patent is hereby corrected as shown below:

alkylen- or -alkenylen-chain having 1 to 3 carbon atoms and an optionally substituted phenyl ring with one or two substituents selected from OH, $NH_2$, F, Cl, $CH_3$, $NO_2$, COOH; an optionally substituted pheny ring with one or two substituents selected from -OH, -Cl, -$CH_3$, -$NO_2$, -COOH or

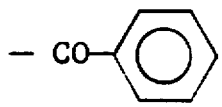

together with the nitrogen atom to which they are bonded form a heterocyclic five- or six membered ring, selected from pyrrolidine, piperidine, piperazine, hexamethyleneimine, morpholine and N-methylpiperazine.

Col. 14, line 5     Delete Claim 6 in its entirety and substitute:

--A process for the production of a compound according to claim 1 which comprises subjecting to catalytic hydrogenation a compound of the formula

UNITED STATES PATENT AND TRADEMARK OFFICE
CERTIFICATE OF CORRECTION

PATENT NO. : 4,536,493        Page 3 of 3

DATED : August 20, 1985

INVENTOR(S) : Bodo Junge, et al.

It is certified that error appears in the above-identified patent and that said Letters Patent is hereby corrected as shown below:

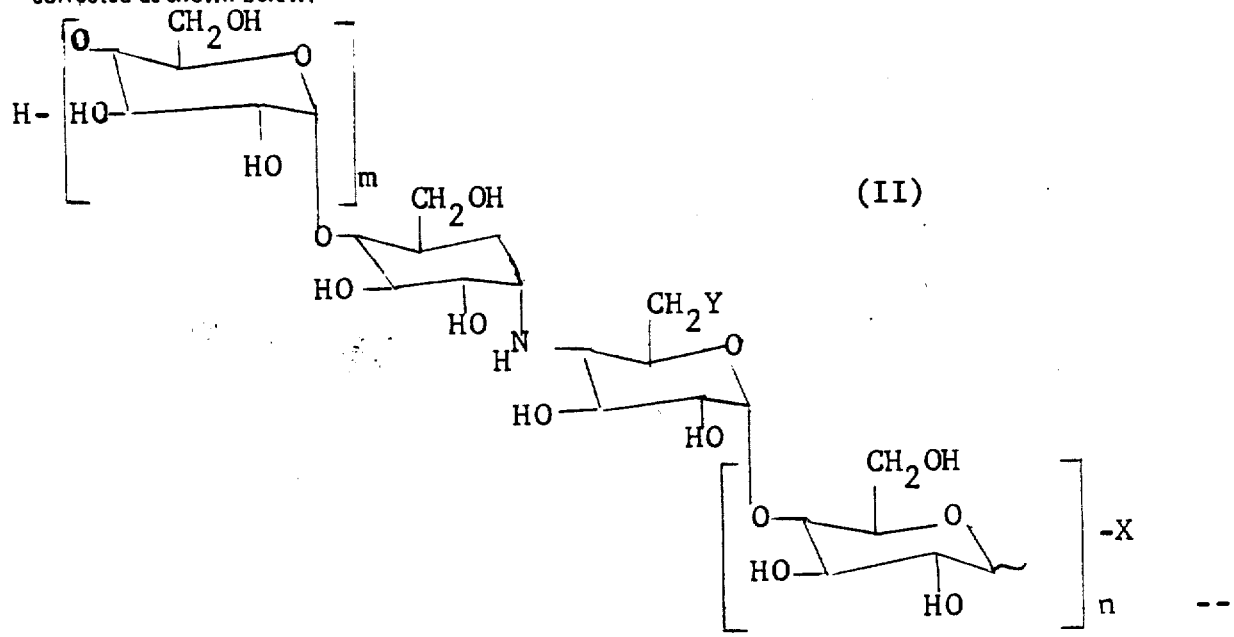

in which
$m$, $n$ and X have the same meanings as in claim 1. --

Signed and Sealed this

Thirtieth Day of December, 1986

Attest:

DONALD J. QUIGG

Attesting Officer    Commissioner of Patents and Trademarks